United States Patent [19]
Hackett

[11] Patent Number: 4,499,777
[45] Date of Patent: Feb. 19, 1985

[54] MOLTEN METAL SAMPLERS

[75] Inventor: Robert J. Hackett, Brookfield, Conn.

[73] Assignee: Haly, Inc., Brookfield, Conn.

[21] Appl. No.: 471,769

[22] Filed: Mar. 3, 1983

[51] Int. Cl.³ .............................................. G01N 1/12
[52] U.S. Cl. .............................. 73/864.56; 73/864.57; 73/864.58
[58] Field of Search ....................... 73/864.53–864.58, 73/DIG. 9; 249/DIG. 4

[56] References Cited

U.S. PATENT DOCUMENTS

| | | | |
|---|---|---|---|
| 3,656,350 | 4/1972 | Collins | 73/DIG. 9 |
| 3,686,949 | 8/1972 | Hacket | 73/864.58 X |
| 3,753,372 | 8/1973 | Collins | 73/DIG. 9 |
| 4,046,016 | 9/1977 | Hacket | 73/864.58 X |
| 4,055,086 | 10/1977 | Collins | 249/DIG. 4 |
| 4,112,772 | 9/1978 | McDevitt | 73/DIG. 9 |

Primary Examiner—Gerald Goldberg
Assistant Examiner—Tom Noland
Attorney, Agent, or Firm—Mattern, Ware, Stoltz & Fressola

[57] ABSTRACT

Highly effective insulated samplers, submerged through floating slag on a body of molten metal, successfully extract, chill and withdraw pin samples and disc samples of specific, predetermined shapes and sizes with high reliability. Deoxidant materials are introduced into the melt just before the sample is taken, whenever required. To eliminate gas bubble inclusions from the chilled samples, ablative deoxidant chambers are employed to carry the deoxidant materials, and are then melted away by the high temperature molten metal being sampled. A disc sampler chill mold provides three rows of vent slots to produce rapid and reliable chilling of disc-shaped samples.

15 Claims, 12 Drawing Figures

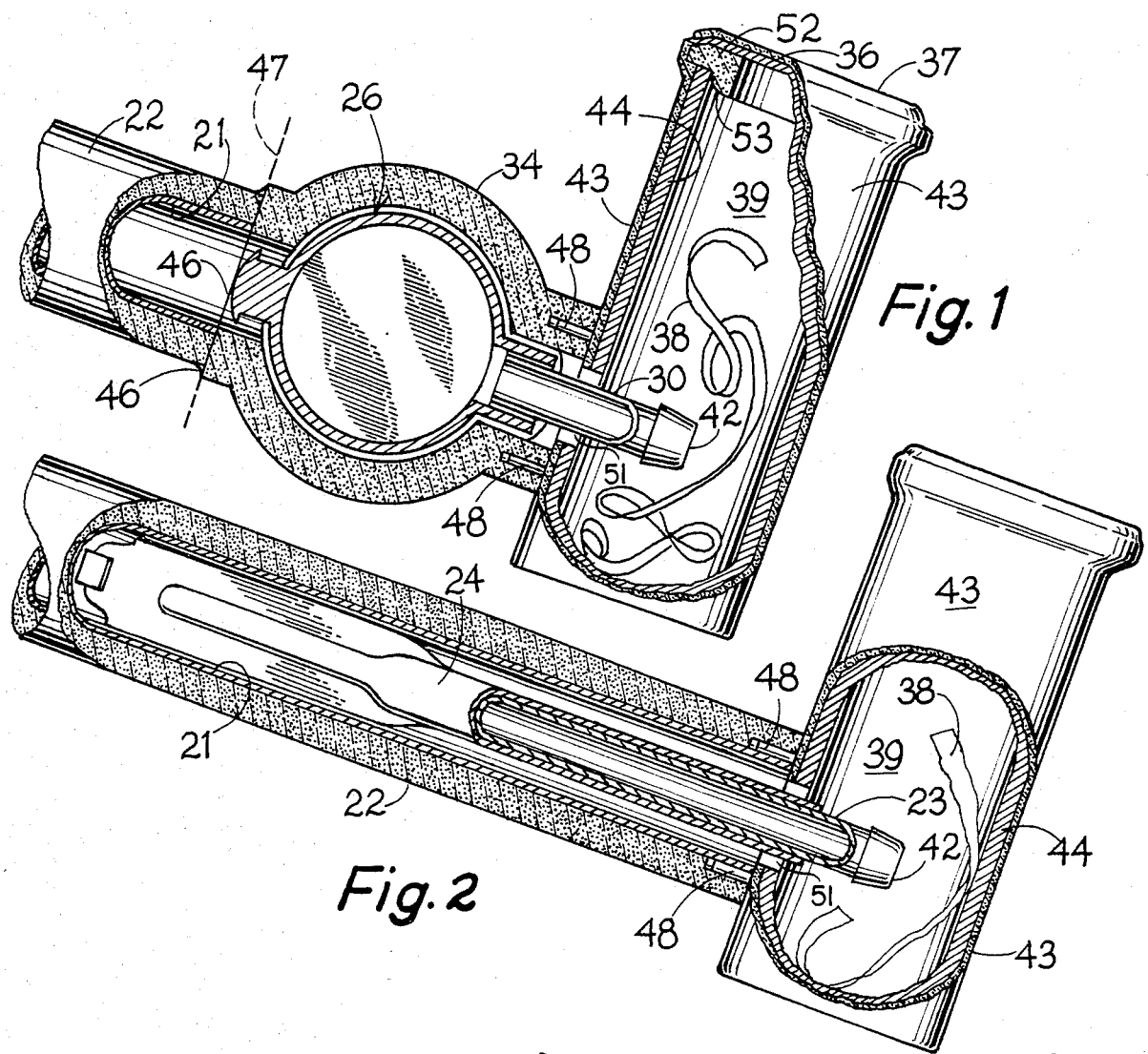
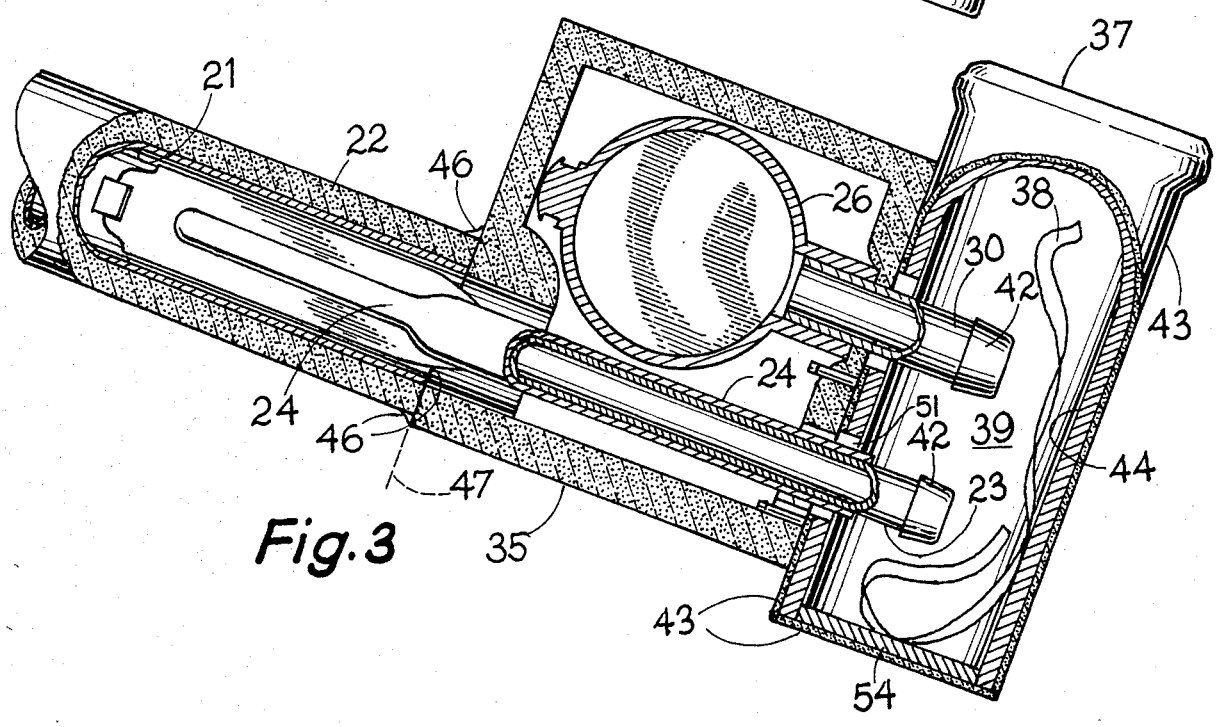

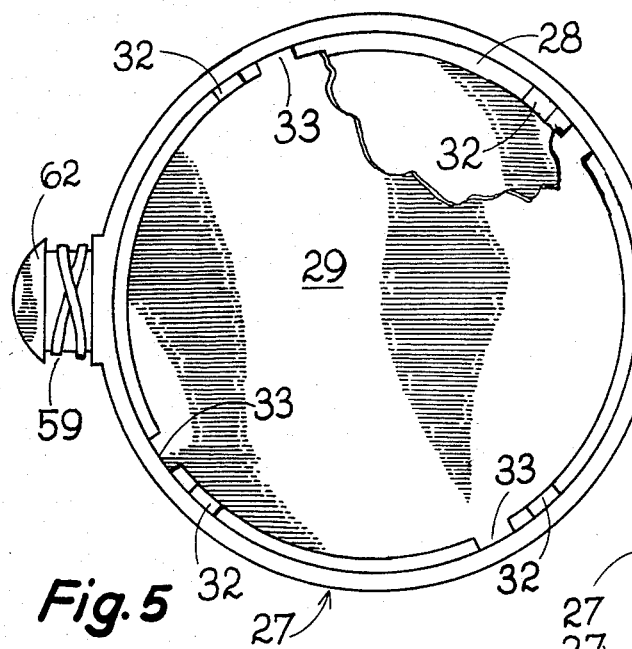
Fig. 5
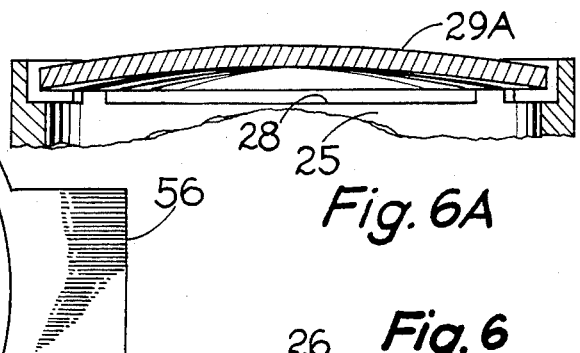
Fig. 6A
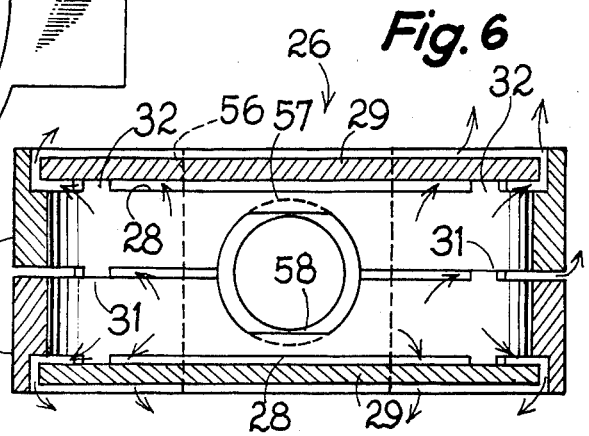
Fig. 6
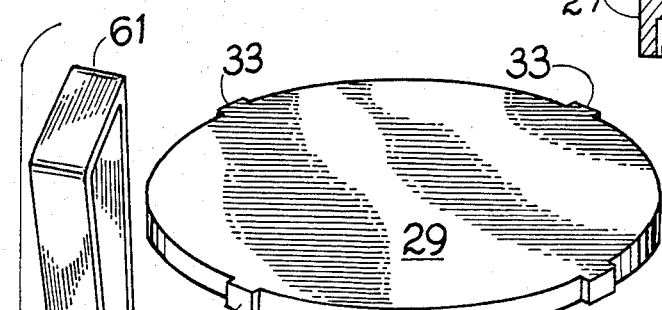
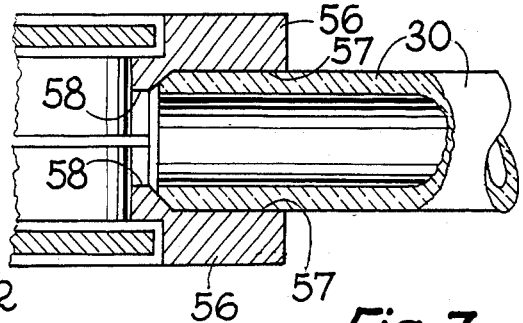
Fig. 7
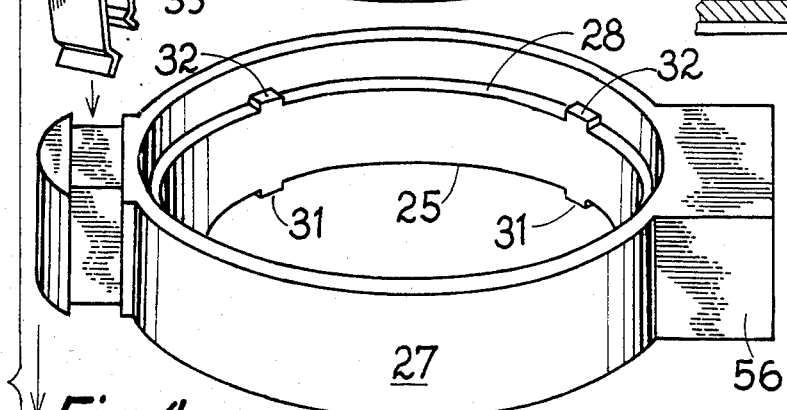
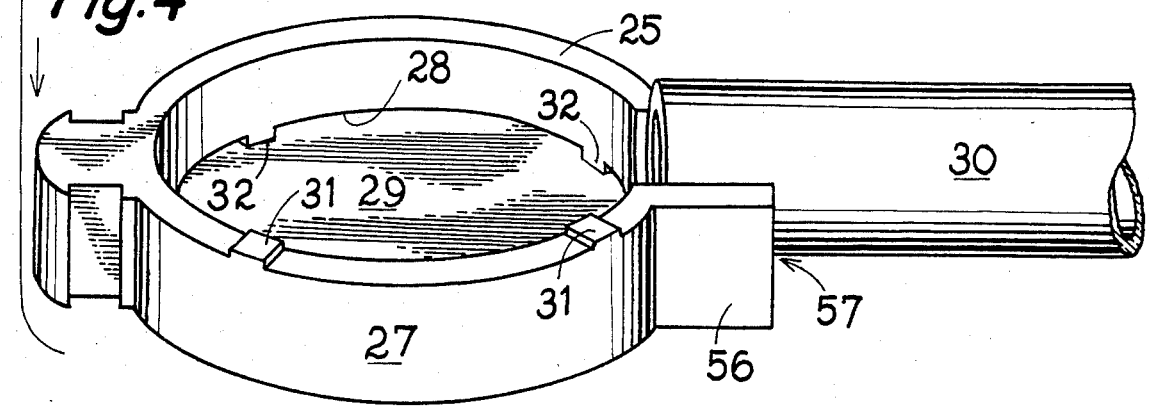
Fig. 4

U.S. Patent  Feb. 19, 1985  Sheet 3 of 3  4,499,777
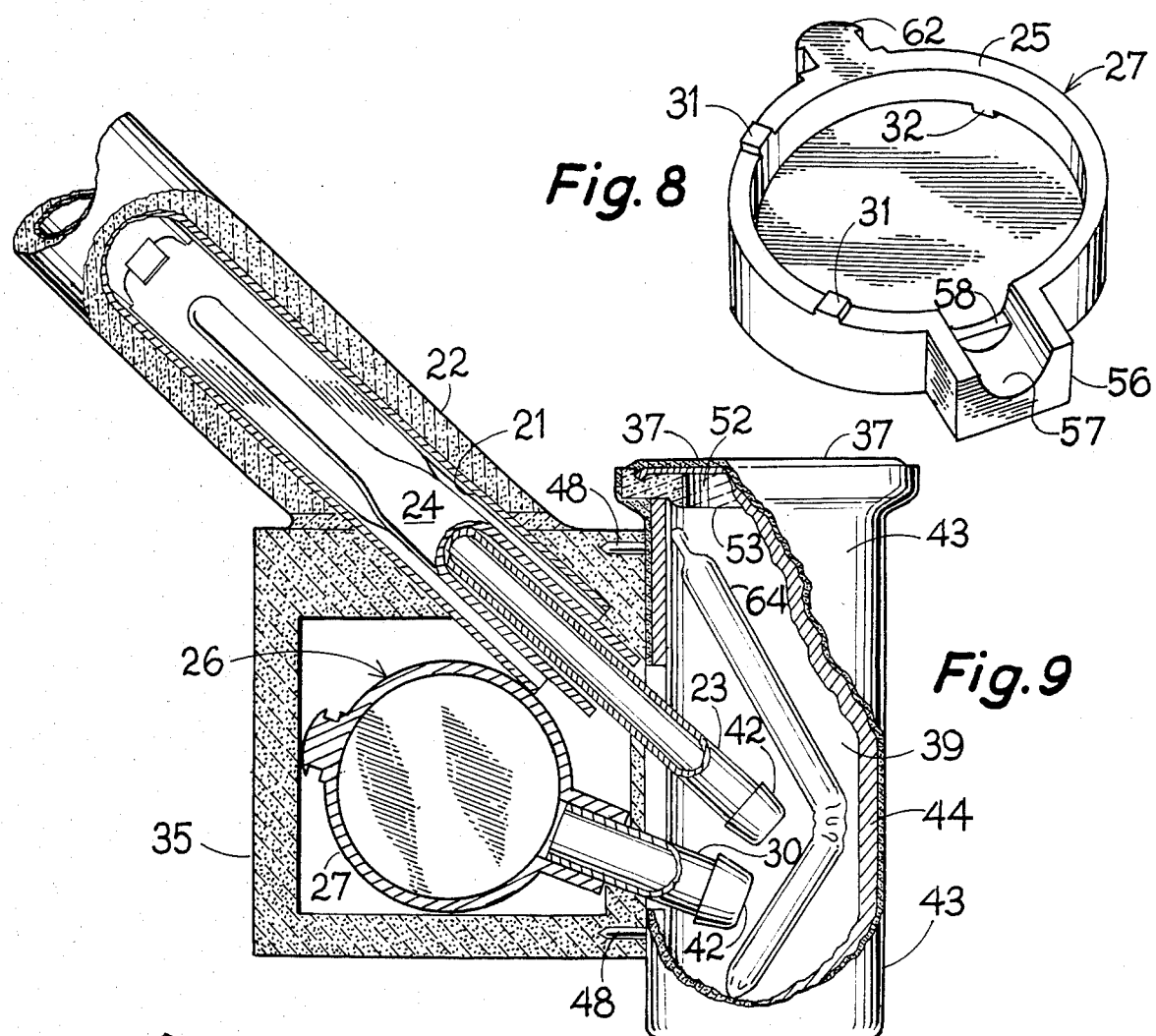
Fig. 8
Fig. 9
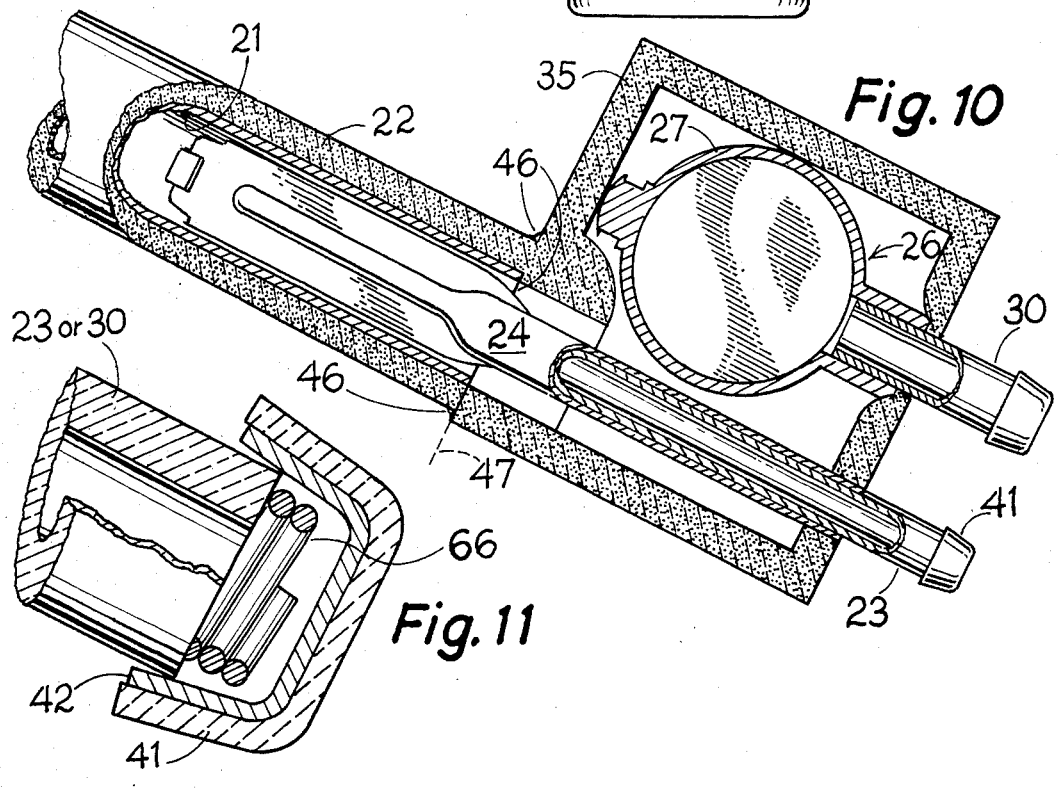
Fig. 10
Fig. 11

MOLTEN METAL SAMPLERS

TECHNICAL FIELD

This invention relates to molten metal sampling devices, and particularly to samplers incorporating insulated metal chill molds mounted at the extreme end of an insulated metal lance tube for plunging immersion through the slag layer into a body of molten metal, a portion of which rushes into the sampler chill-mold cavity which is then quickly withdrawn from the melt and quenched if necessary, producing a solidified sample of the molten metal.

BACKGROUND ART

Many different types and shapes of samplers for molten metal have been developed or proposed in recent years. These include the samplers disclosed in my previous U.S. Pat. Nos. 3,457,790; 3,452,602; 3,686,949; and 4,046,016; and the foamed ceramic or castable silicate compositions described in my U.S. Pat. No. 3,561,494 provide excellent heat insulating coatings protecting samplers and lance tubes from the high temperature molten metal during the sampling operation, and assuring proper chilling of the melt samples.

A sampler for molten metal must provide a sampling chamber or cavity enclosed inside a hollow chill mold, which is provided with slots or vents capable of venting the air displaced by the inrushing molten metal. Surrounding insulating material, such as a foamed ceramic coating, preserves the chill mold at a temperature far below that of the molten metal for a period long enough to chill the inrushing molten sample to the consistency of slush. The sampler is then removed from the melt, and cooling is continued by exposure to the atmosphere at room temperature, or to a quenching bath of water or liquid nitrogen, for example.

The samplers of my previous patents produce reliable and homogeneous samples in the deep immersion sampling operations in which they are customarily used or in killed steel sampling operations requiring no deoxidizing treatment. When a high oxygen content must be counteracted, or a deoxidized sample must be taken from a shallower melt, as in a continuous caster operation, high reliability, approaching one hundred percent, can be achieved utilizing the features and combinations of features characterizing the samplers of the present invention. Entrained gas bubbles, forming inclusions or voids, are virtually eliminated by these samplers. Metallic deoxidants in strip, wire or powdered form are thoroughly dispersed just prior to the sampling operation, and the inflowing surge of molten metal entering the sampling chamber inside the chill mold is virtually unimpeded. The unique vent slots release the air displaced by the entering sample with unusual effectiveness. The high precision chill molds produce precisely dimensioned samples suitable for spectrophotometric analysis and other metallurigcal tests with nearly perfect reliability, in the precise dimensions desired with smooth surfaces and with homogeneous compositions, accurately representing the composition of the metal.

Accordingly, the principal object of the present invention is to provide a highly efficient molten metal sampler capable of producing homogeneous and representative samples taken from the central portion of a body of molten metal, chilled and solidified for metallurgical testing with a high degree of reproducibility and reliability.

Another object of the invention is to provide such molten metal samplers incorporating metal chill molds providing a plurality of rows of vent slots to release air displaced by inrushing molten metal.

A further object of the invention is to provide such molten metal samplers which are easily detached from the lance tube for examination, after the chilled sample is removed from the melt.

Another object of the invention is to provide such molten metal samplers in which the chill mold parts are formed by powder metallurgy techniques, achieving high precision with a minimum of machining operations.

Still another object of the invention is to provide such molten metal samplers in which deoxidant material is carried in a sealed ablative deoxidant chamber just outside the entrance portal of the sampler itself, with the sealed entrance cap of the deoxidant chamber being adapted to melt, following exposure to the high central temperatures of the body of molten metal, admitting the melt and releasing the displaced air in an upward direction with consequent turbulent mixing of the melt and deoxidant material carried in the chamber to produce thorough deoxidizing just prior to entrance of the molten metal into the sampler's chill mold, with the deoxidant chamber walls being designed to be melted and carried away, leaving its ceramic insulating coating forming part of the floating slag layer as the sampling operation is completed.

A further object of the invention is to provide such molten metal samplers capable of forming two samples simultaneously, both of which are filled by the deoxidized molten metal in the deoxidant chamber prior to its disappearance from the sampler.

Another object is to provide a variable or adjustable cooling rate by using preselected chilling discs of selected thickness, which allow sampling at predetermined higher or lower temperatures, reliably delaying the freezing of the sample until the sampler is filled.

Other objects of the invention will in part be obvious and will in part appear hereinafter.

The invention accordingly comprises the features of construction, combinations of elements and arrangement of parts which will be exemplified in the constructions hereinafter set forth, and the scope of the invention will be indicated in the claims.

BRIEF DISCLOSURE OF THE INVENTION

The molten metal samplers of the present invention preferably incorporate a substantially cylindrical enclosure surrounding a deoxidant chamber and having an open entrance portal facing upward in the immersed sampling position of the sampler. This deoxidant chamber enclosure is preferably formed of relatively thick sheet steel, having its lower end enclosed, and its upward-facing portal is provided with an annular ceramic rim guard surrounding a large central aperture which is spanned by a thin sheet metal cap cemented in place. The steel shell and the metal cap are enclosed in a thin coating of foamed ceramic heat insulating material, providing just enough insulation to protect the cap and the steel shell during their descent through the slag layer floating on top of the body of molten metal being sampled. A comparable but much thicker foamed ceramic insulating layer encloses the chill mold sampler itself, and the cylindrical steel lance tube, and the chill mold and lance tube are thus protected by their thick insulating layer of foamed ceramic for a much longer period of time. The thin steel cap is melted first by the extremely high temperature body of molten metal in which the sampler assembly is immersed, and the melt rushing through the central aperture in the annular ceramic rim guard surrounds and melts the deoxidant material inside the chamber, while at the same time displacing the air therefrom upward toward the free surface of the melt. The turbulent mixing deoxidation is virtually complete when the protective cover is melted from the lance tube portal exposed inside the chamber, and the deoxidized molten sample then rushes into the chill mold where it is partially solidified.

At the same time, the thin walled steel shell which surrounded the deoxidant chamber is melting and is carried away by the melt as the sampler is removed from the molten metal in the same manner that an ablative heat shield is carried away by frictional engagement with the atmosphere as a spacecraft returns from outer space through the atmosphere for a planetary landing. The deoxidant chamber can therefore be called an "ablative" deoxidant chamber which serves its temporary purpose in delivering the deoxidant material to the desired location, and is then carried away as the sampling operation is completed, exposing the sample in its chill mold for easy and convenient removal from the sampler after cooling.

Another preferred feature of the sampler assemblies of this invention is a unique form of disc sample chill mold, having two flat ring-shaped cylindrical mold halves with flat removable cover discs of predetermined thickness spanning their outer ends and spaced therefrom by the width of a predetermined slot, creating a vent slot of significant width around the entire periphery of each cover disc. The two cylindrical mold halves are held in facing engagement with their open inner ends juxtaposed and substantially spaced apart by raised lands, producing a comparable peripheral slot of significant width around the central equator of the flat cylindrical disc sample chill mold.

The provision of deoxidant materials in the form of ribbons, wires, helical coils or metallic powders enclosed in paper tubes, positioned inside a slag cover at the entrance portal of the chill mold itself, produces a uniform, homogeneous sample accurately representing the composition of the molten material being sampled.

For a fuller understanding of the nature and objects of the invention, reference should be had to the following detailed description taken in connection with the accompanying drawings.

A BRIEF DESCRIPTION OF THE DRAWINGS

FIGS. 1, 2 and 3 are fragmentary, side elevation views, partially broken away, showing the chill mold and the ablative deoxidant chamber associated therewith in preferred embodiments of the molten melt samplers of the present invention.

FIG. 4 is an exploded perspective view of a disc sample chill mold of the present invention, showing its component parts, the ring-shaped cylindrical mold halves and the associated cover disc installed in each mold half.

FIG. 5 is a top plan view of the disc sample chill mold, partially broken away, showing both cover discs installed in their ring-shaped chill mold halves.

FIG. 6 is a cross-sectional end elevation view of the disc sample chill mold of FIGS. 4 and 5, showing the three groups of peripheral vent slots facilitating the escape of air displaced therefrom by inrushing molten metal.

FIG. 6A is a corresponding fragmentary elevation view of a modified chill mold of the same kind, showing its convex gently arched cover disc.

FIG. 7 is a fragmentary cross-sectional side elevation view of the chill mold halves and cover discs of FIG. 6, illustrating their cooperation with a cylindrical chill mold portal tube, preferably formed of quartz glass.

FIG. 8 is a perspective view of a ring-shaped chill mold half with its cover disc plate.

FIG. 9 is a fragmentary sectional side elevation view, partially broken away, showing a disc sample chill mold and a pin sample chill mold with their axes converging in an ablative deoxidant chamber in which powdered deoxidant material is positioned inside a paper tube ready for the sampling operation.

FIG. 10 is a fragmentary sectional side elevation view, partially broken away, showing a disc sample chill mold and a pin sample chill mold having no separate ablative deoxidant chamber, but with their deoxidant materials positioned inside their slag cover cap, and FIG. 11 is a greatly enlarged cross-sectional side elevation view of the slag cover cap cemented to the entrance portal of one of the chill molds shown in FIG. 10, with a helical coil of metallic wire deoxidant material enclosed inside the slag cover cap.

BEST MODE FOR CARRYING OUT THE INVENTION

The molten metal samplers shown in FIGS. 1, 2, 3 and 9 exemplify the preferred embodiments of the present invention. In each of these embodiments, the sampler assembly is installed at the end of a hollow cylindrical steel lance tube 21, having a sturdy layer 22 of laminated paper or foamed ceramic insulation surrounding its entire periphery and serving to protect the lance tube 21 from the heat of the molten metal in which it is immersed. The sampler itself incorporates a sample chill mold, which may be formed as a long hollow ceramic pin sample mold 23, formed as a tube of quartz glass for example, and closely embraced inside a slotted riser vent assembly 24 supporting the chill mold tube and venting from it into the interior of lance tube 21 the air displaced by the inflowing molten metal filling the sampler. Suitable slotted riser vents are shown as vents 43 and 47 in my U.S. Pat. No. 4,046,016, and as vents 20 in my co-pending U.S. Pat. Application Ser. No. 445,002, filed Nov. 29, 1982, now U.S. Pat. No. 4,453,424.

FIGS. 1, 3 and 9 show the different shape of chill mold whose component parts are shown in more detail in FIGS. 4, 5, 6 and 7. This is a disc sampler chill mold 26 formed by two ring-shaped mold halves 27, each having an internal, stepped outward-facing shelf 28 on which a cover disc plate 29 is superimposed in peripherally spaced relationship, providing a long vent slot around its entire periphery. The disc sampler mold halves 27 are provided with central rims facing each other and spaced apart by raised lands 31 formed directly on the facing rims 25 of the two disc sampler mold halves 27, and thereby forming a peripheral vent slot between these two halves in their assembled position.

As shown in FIGS. 4, 5 and 6, the mold halves 27 are preferably identical, with two lands 31 formed only on one side of the rim 25, the 180 degree sector extending clockwise from entrance portal tube 30. When the two mold halves are juxtaposed embracing portal tube 30 with their respective rims 25 facing, the counterclockwise 180 degree sector of rim 25 of the lower mold half 27 with no lands 31 protruding therefrom receives the lands 31 depending from the overlying rim 25 of the upper facing mold half 27, spacing the rims 25—25 apart to form a vent slot around substantially the entire periphery of the mated pair of mold halves, as shown in FIG. 6.

Similar lands 32 are formed on the stepped shelf 28 which faces outward toward the cover disc plate 29, and disc plate 29 is seated upon these lands 32 spacing it above the shelf 28. Similarly, the rim of disc 29 is undersized with a smaller outside diameter than the inside diameter of the mold half 27 into which it is assembled. The rim of disc 29 is provided with several protruding lands 33, best shown in FIG. 4, and two pairs of these lands 33 protrude diametrically opposite each other on the rim of disc 29, with an outside diameter permitting disc 29 to fit inside the outer face opening of the ring-shaped mold half 27 in the assembled position shown in FIGS. 5, 6 and 7. The lands 33 serve to space the disc 29 peripherally away from the interior wall of mold half 27, thereby forming with lands 32 a peripheral slot or passageway around the entire outer circumference of each mold half 27. Both the upper mold half and the lower mold half are provided with similar slotted vent means formed by lands 32 and 33 around their entire peripheries, which supplement the peripheral vent slot formed by lands 31, encircling the equatorial region of the assembly of the two mating mold halves 27. Thus, as shown in FIG. 6, there are preferably three peripheral vent slots encircling the entire disc sampler 26.

As shown in FIG. 6A, in one embodiment the cover disc 29A is gently arched outward to form slightly bulging or convex circular end surfaces on the flat, cylindrical disc sample formed inside the chill mold 26. As the molten sample chills and solidifies, it tends to draw inward from the interior center of the cover discs, leaving concave end surfaces, which must be ground flat for metallurgical testing. Slightly convex cover discs 29A counteract this tendency, and minimize any grinding required to prepare the disc for spectrophotometry or X-ray laboratory testing. Cover discs 29 of different thicknesses are selected to increase or reduce the chilling time, accommodating different melt temperatures, and consequently producing samples with the smoothest, flattest end test surfaces possible.

INSULATED SAMPLE ENCLOSURE

To protect the chill mold samplers, whether of the pin sample configuration 24 or the disc sampler configuration 26, the samplers are enclosed within a thick body of foamed ceramic material, like that disclosed in my U.S. Pat. No. 3,561,494. This may take the form of a rectangular enclosure 35, as shown in FIGS. 3, 9 and 10, and both samplers can be installed in a single such rectangular enclosure 35.

When a single chill mold pin sampler is employed, it may be mounted directly inside the heat insulated lance tube 21, as shown in FIG. 2, or in the case of the single disc sampler 26, it may be mounted in its own specially shaped cylindrical enclosure 34, as shown in FIG. 1. In all of these cases, the thick body of foamed ceramic material protects the chill mold sampler against the heat of the melt, assuring that it will not be eroded or melted by the heat, and that its initial room temperature will allow it to be immersed in the melt while maintaining a sufficient temperature differential to chill the inrushing molten metal and form a partially solidified sample during the sampler operation and before the sampler is withdrawn from the melt.

As shown in FIGS. 6 and 8, each mold half 27 is provided with a portal trough 56, a hollow semi-cylindrical groove formed in a radially projecting portal block 57 protruding radially from the outer wall surface of mold half 27. A low rim or beveled flange 58 protrudes into trough 56 at the threshold where the trough 56 opens into the interior of the mold half 27, forming a stop against which the inner end of portal tube 30 abuts when it is inserted and cemented into trough 56. As shown in FIG. 6, flange 58 is lower than the wall thickness of portal tube 30, assuring that the stream of molten metal entering the chill mold will not be obstructed by flange 58.

Mold halves 27—27 are secured together in their juxtaposed mated position, as shown in FIGS. 4, 5 and 6, by a rubber band 59 or a resilient U-shaped metal clip 61 embracing a pair of aligned clamping flanges 62, each protruding radially from the outer wall surface of one of the mold halves 27 opposite portal block 57.

If desired, a helical coil 66 of metallic deoxidant, such as aluminum, titanium, zirconium or magnesium, having a diameter roughly corresponding to that of portal tube 23 or 30 may be positioned inside metal cap 42, which will itself be enclosed inside a protective paper cap 41, as shown in FIGS. 10 and 11 if it is not protected inside a pre-cooling chamber 39 of the kind shown in FIGS. 1, 2, 3 and 9.

ABLATIVE COOLING AND DEOXIDANT CHAMBER

The principal operation occurring in blast furnace or basic oxygen furnace treatment of iron ore and scrap to convert them to steel is the introduction of oxygen to combine with the carbon normally present and reduce the carbon content of the melt toward that desired for the resulting steel composition. The presence of excess oxygen in the melt creates a serious risk of bubble inclusions or voids in the interior of any small solidified sample taken from the melt, and deoxidation of the sample prior to its solidification in the sampler is therefore required. Deoxidation is achieved by distribution throughout the molten sample of a metallic deoxidant material, such as aluminum zirconium, magnesium or titanium, in finely divided powder form or as ribbon or wire, such as a helical coil spring shape, positioned in a deoxidant chamber where the portion of the melt being sampled can be deoxidized just prior to the solidification of the sample in the chill mold.

It has now been discovered that an upwardly facing chamber 39, having an overlying upwardly opening entrance portal protected by a thin metallic cap 36 having only a thin heat insulating layer protecting it from the high temperature of the melt, serves exceptionally well to contain the deoxidant material and to deliver it at the precise location required. FIGS. 1, 2, 3 and 9 show examples of these chambers.

My U.S. Pat. No. 3,686,949 discloses the structure and operation of my "Big Dipper" Sampler, manufactured and sold by my licensee, Haly, Inc., of Brookfield, Conn. FIGS. 5, 6, 7 and 16 of that patent show the large deoxidant bowl or chamber of that Sampler, communicating directly with a pin sample mold 64 as shown in FIGS. 8 and 14 of that patent. In that prior patent and my "Big Dipper" Samplers, there was no isolation or barrier between the deoxidant chamber and the pin sample chill mold. Furthermore, those earlier deoxidant bowls or chambers were heavily insulated by a thick refractory coating of foamed ceramic or multiple-layered paper, leaving the chambers intact after sampling was completed, and blocking access to the chilled sample.

My U.S. Pat. No. 4,046,016 shows similar heavily-insulated deoxidant portal chambers, two of which in FIGS. 11 and 18A of that patent have upward-facing openings. Being formed of thick-walled, cast, foamed ceramic, these chambers trap the molten metal if they are withdrawn upright from the melt, and would require a tilting, dumping twist during withdrawal to release the entrapped melt unless they incorporate the drain vents 76B, shown in that U.S. Pat. No. 4,046,016.

I have now discovered that for best results, the cooling and deoxidant chamber must be virtually un-insulated, and a barrier should also be installed to block the chill mold from the deoxidizing operation until deoxidizing has time for completion. In many cases, particularly with high oxygen contents, such isolation successfully produces homogeneous, representative samples, with no internal voids or discontinuities, and with virtually complete reliablity and reproducibility. Temporary isolation of the inrushing molten metal completes deoxidation, and the deoxidized metal is then ready for molding into a chilled sample.

The thin metal cap 36 and the thin insulating coating 37 overlying the cap, such as foamed ceramic, protect the deoxidant material 38 inside the chamber 39 during the plunging immersion of the sampler through the slag layer floating on the surface of the molten metal to be sampled. As the sampler reaches the desired sampling depth, the heat of the melt melts the thin protective metal cover 36. The melt rushes downward through the upward-facing portal of the deoxidant chamber 39 to displace the air trapped therein and to surround and melt the metallic deoxidant 38 in swirling, mixing action.

This molten metal rushing into the deoxidant chamber 39 thus has a predetermined short period of time to complete its own deoxidation before its elevated temperature melts the metal cap 42 protecting the sampler chill mold portal 23 or 30, and the molten sample now deoxidized rushes into the chill mold which is maintained cool enough by its thick coating of insulating material 22, 33 or 34, to chill the sample, at least partially solidifying it.

An added advantage of chamber 39 results even when deoxidant is not required: the inrushing molten metal is cooled enough to make it slightly thick and viscous, assuring its smooth non-turbulent entry into sampler entrance portals 23 and 30 and creating uniform homogeneous samples with no voids or discontinuities. Thus, deoxidant 38 may be omitted from the sampler of FIG. 3, for example, when deoxidizing is not required, and chamber 39 cooperates with chill molds 23 and 26 to produce high quality chilled samples of the melt.

The thin insulating coating 43 covers the exterior surface of the cylindrical metal wall 44 enclosing the deoxidant chamber, protecting the chamber 39 until cap 36 melts. Then the chamber's thin walls 44 heated by the entering molten metal rapidly soften, and they melt away as the sampling operation is completed, and before the sampler is withdrawn from the melt, thus leaving the sampler exposed for quick access to the chilled sample. No drain vents are required, and no special manipulation is needed to achieve excellent and freely acessible samples.

The temporary isolation of chill mold from deoxidizing chamber by metal cap 42, and the thin insulating coating on cap 36 and walls 44 defining chamber 39, thus cooperate with the other structural features of the sampler assembly to produce unusually reliable samples, and to expose them for ready accessibility when sampling is completed.

QUICK RELEASE, BREAKAWAY CONSTRUCTION

The samplers of this invention are firmly secured to the distal end of the lance tube 21 in different ways. In the sampler assembly shown in FIG. 1, the disc sampler 26 in its thick insulating enclosure 34 is secured to lance tube 21 by cement embracing the abutting junction of enclosure 34 and the foamed ceramic coating 22 encircling lance tube 31. Cement 46 forms a thin film joining the facing abutting surfaces of these two foamed ceramic enclosures 22 and 34 and provides an external fillet 46 at their junction. A comparable cement layer and fillet 46 is shown in FIG. 3, bonding the thick rectangular foamed ceramic enclosure 35 to the abutting end face of foamed ceramic coating 22 on lance 21. The same is true of the cement coating and fillet 46 shown in FIG. 10.

After the sampling operation is completed, and the sampler is withdrawn from the melt, a sharp sidewise blow on the sampler will separate it from the lance tube 21 at the dotted cement junction line 47 shown in FIGS. 1, 3 and 10, shattering the cement bond 46 for quick breakaway release of the sampler.

As shown in FIGS. 1, 2, 3 and 9, the upwardly facing deoxidant chamber 39 is formed within cylindrical wall 44, which is preferably provided with two radially protruding pins 48, extending outward from the outer surface of the cylindrical steel wall 44 through the thin insulating coating 43 into mating holes formed in the end of the thick body of foamed ceramic insulation 22 surrounding lance tube 21 or body 34 surrounding disc sampler 26 or rectangular enclosure 35 surrounding pin sampler 23 and its slotted vent tube 24 and the disc sampler 26 with its portal tube 30. Pins 48 protrude from the outer surface of wall 44 at points adjacent to side aperture means 51 formed in wall 44 to accommodate the sampler portal tubes 23 and 30, and the pins 48 tend to stabilize the deoxidant chamber, which is also cemented to the facing ends of the foamed ceramic insulation material 22, 34 or 35. Pins 48 may be headed to provide enlarged flat surfaces suitable for welding to the outer surface of wall 44.

If desired, the thin foamed ceramic layer 43 surrounding walls 44 may be cast or molded integrally with the thicker block of foamed ceramic insulation surrounding the chill mold parts, such as enclosure 34 or 35, preferably in two mating halves suitable for assembly embracing the steel parts, with ceramic cement then being used to join the two halves together. Such integral molded ceramic enclosures may omit pins 48 if desired.

ENLARGED CERAMIC PORTAL RIM OF DEOXIDANT CHAMBER

Underlying the thin metallic cap 36 around the rim of the upward-facing open portal end of cylindrical wall 44 surrounding deoxidant chamber 39 is an annular ceramic rim guard 52, having a downward facing ledge abutting and cemented to the upward-facing rim of the cylindrical steel chamber wall portion 44, and having a depending interior lip or flange 53 dimensioned to telescope a short distance inside the mouth of the upward-facing portal of the cylindrical steel wall 44. Ceramic rim guard 52, shown in FIG. 1, extends only a short distance beyond the outer periphery of the steel wall 44, and the thin ceramic insulation coatings 37 and 43 together cover the thin sheet metal cap 36 and ceramic rim guard 52 to provide a totally ceramic-coated body, as shown in FIGS. 2 and 3.

In the form of the ceramic rim guard 52 shown in FIG. 9, its outer periphery extends radially further beyond the upward-facing portal of the steel wall 44, and is provided with an upper rim groove encircling its upper periphery and receiving the downturned rim of the thin steel cap 36.

In all preferred forms of the sampler assemblies of this invention, the ceramic rim guard 52 has a substantial cross-sectional area and significant volume, presenting to the melt a thick heat insulation layer than thin coating 43, for example. Rim guard 52 thus serves to protect the upper end of cylindrical steel wall 43 from erosion or premature melting by the molten metal into which the sampler has been plunged. In the absence of such a protective rim guard 52, the upper end of the steel wall 44 might reach the elevated melt temperature so rapidly that it would begin to melt and contribute its own composition to the sample being taken, which would thereby be rendered less representative of the molten metal being sampled. Ceramic rim guard 52 thus enhances the metallurgical accuracy of the compositions of the melt sample being secured, and avoids contamination by the sampler itself.

It has been found that the most dependably reliable samples are taken from the lower, central portion of chamber 39, where the intake portals 23 and 30 of the samplers are positioned with their protective metal caps 42 exposed to the molten metal. Caps 42 are designed merely to delay the entry of the molten metal in chamber 39 long enough to allow the deoxidizing process to proceed to completion in chamber 39. As the temperature of the cap 42 rises rapidly upon exposure to the molten metal in chamber 39, cap 42 softens and melts, allowing the now deoxidized metal filling chamber 39 to flow into tube 23 or tube 30 or both, to be chilled in the chill mold after deoxidizing is completed. Samples taken from non-central portions of chamber 39 or from upper portions of chamber 39 may be found adequate, but there is a possibility that incomplete deoxidation may reduce the accuracy of the constituent composition of the resulting sample as a representative specimen of the molten metal.

To obtain the maximum advantage of the highly effective deoxidizing operation, the sampling zone located centrally in chamber 39 and slightly below its midpoint may provide the molten metal in roughly equal proportions entering two different sampler chill molds. FIG. 9 shows pin sample chill mold 23 and disc sample chill mold 26 with their entrance portals 23 and 30 positioned on converging axes, both aimed toward the preferred central region below the midpoint of chamber 39 from which the most accurate representative samples are drawn.

FIG. 9 also shows a tubular paper container of finely divided metallic deoxidant, such as a "soda straw" with sealed ends enclosing powdered aluminum or magnesium as shown in FIGS. 19 and 20 of my U.S. Pat. No. 3,686,949.

It will thus be seen that the objects set forth above, among those made apparent from the preceding description, are efficiently attained and, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

I claim:

1. A chill mold assembly for collecting, chilling and withdrawing a flat cylindrical sample from a body of molten metal, comprising:
   A. a ceramic portal tube,
   B. two juxtaposable facing mold havles, each having a ring-shaped outer wall terminated by
      1. a substantially flat proximal rim incorporating raised land means,
      2. a distal rim,
      3. and means forming a portal flange extending radially outwardly from the outer wall and having a concave trough formed therein extending through the outer wall and the flange and opening toward the proximal rim,
   C. a cover disc positioned spanning the outer wall of each mold half near the distal rim
      1. with protruding land means positioned between the cover disc and the mold half, maintaining a vent slot of predetermined width around the periphery of the cover disc,
   D. and clamping means cooperating with the facing chill mold halves to secure them together with the raised land means of the proximal rims spacing the proximal rims apart to provide a peripheral equatorial vent slot therebetween, and with their concave troughs facingly embracing the ceramic portal tube about an inner end thereof, whereby a chill mold for flat cylindrical samples of solidified metal is achieved having three vent slots of predetermined minimum width encircling its periphery.

2. The chill mold assembly defined by claim 1, wherein each cover disc is convexly arched away from the proximal rims, whereby central shrinkage of the cooling molten metal sample is compensated for.

3. The chill mold assembly defined by claim 1, wherein the mold halves are formed of sintered powdered metal.

4. The chill mold assembly defined by claim 1, wherein the clamping means is a spring clip resiliently embracing both of the two mold halves.

5. The chill mold assembly defined by claim 1, wherein the clamping means comprises a stretched elastomer band.

6. The chill mold assembly defined by claim 1, further including a metallic cap enclosing the outer end of the portal tube, and having a body of metallic deoxidant material positioned between the portal tube's outer end and the metallic cap.

7. The chill mold assembly defined by claim 1, further including

A. a heat-insulated, hollow, elongated lance having a sampling end and an open handle end exposed to the atmosphere, B. a hollow, heat-insulated enclosure surrounding the chill mold assembly with its portal tube protruding therethrough, and having a vent opening aligned with the sampling end of the lance tube through which the vent slots communicate with the atmosphere, and C. means joining the enclosure to the sampling end of the hollow lance with the portal tube protruding for immersion in the molten metal.

8. A chill mold assembly for collecting, chilling and withdrawing a flat cylindrical sample from a body of molten metal, comprising A. a ceramic portal tube, B. two juxtaposable facing mold halves, each having
 a a ring-shaped outer wall terminated by
 1. a substantially flat proximal rim incorporating at least two raised lands,
 2. a distal rim,
 3. and means forming a portal flange extending radially outwardly from the outer wall and having a concave trough formed therein extending through the outer wall and the flange and opening toward the proximal rim,
 4. with means forming a peripheral stepped internal ledge near the distal rim, with the outer wall being radially thinner between the ledge and the distal rim than between the ledge and the proximal rim, C. a cover disc positioned spanning the outer wall of each mold half near the ledge and having an outer diameter less than the inner diameter of the distal rim and greater than the inner diameter of the ledge means,
 1. with protruding land means positioned between the outer edge of the cover disc and the side wall, and between the cover disc and the ledge, maintaining a vent slot of predetermined width around the periphery of the cover disc, D. and clamping means cooperating with the facing chill mold halves to secure them together with the raised lands of the proximal rims spacing the proximal rims apart to provide a peripheral equatorial vent slot therebetween, and with their concave troughs facingly embracing the ceramic portal tube whereby a chill mold for flat cylindrical samples of solidified metal is achieved having three vent slots of predetermined minimum width encircling its periphery.

9. A chill mold assembly for collecting, chilling and withdrawing a sample from a body of molten metal having an overlying slag layer, comprising A. an elongated, hollow, heat-insulated lance tube having a sampling end and an open handle and exposed to the atmosphere, B. a slot-vented chill mold secured to the sampling end of the lance and having an open protruding portal end protected by a thin metal cap and a vented end exposed to the hollow interior of the lance's sampling end, C. heat-insulating means isolating the slot-vented chill mold from the surround, and D. a substantially less insulated metal-walled ablative pre-cooling chamber
 (1) secured to the heat-insulating means isolating the chill mold,
 (2) surrounding the chill mold's portal end,
 (3) and having an opening, upward-facing during collection, and protected by a thin metal slag cover, and a thin foamed ceramic heat insulating coating surrounding the exterior surface of the chamber walls having a thickness substantially less than the thickness of the heat-insulating means isolating the chill mold, whereby the metal slag cover melts only after the pre-cooling chamber surrounding the chill mold's portal end is immersed through the slag layer into the body of molten metal, which fills the pre-cooling chamber by displacing air therefrom through its upward-facing opening, melting the thin metal cap protecting the chill mold portal while surrendering heat to the metal-walled chamber, thereby filling the chill mold with pre-cooled fluid metal as the metal-walled chamber continues to absorb heat from the melt and reaches its own melting point, to be swept away as the heat-insulated lance and chill mold are withdrawn from the molten metal.

10. The chill mold assembly defined in claim 9, wherein the thin metal slag cover is formed of a deoxidant metal.

11. The chill mold assembly defined in claim 9, wherein a body of metal deoxidant having a small cross-sectional area compared to the surface area of the ablative pre-cooling chamber is positioned inside the pre-cooling chamber.

12. The chill mold assembly defined in claim 9, further including a thick annular ceramic rim guard encircling the upward-facing opening of the pre-cooling chamber, whereby the melting of the opening rim portion of the metal-walled chamber is delayed until its interior is filled with molten metal.

13. The chill mold assembly defined in claim 9, wherein the metal-walled pre-cooling chamber and the thin metal slag cover are both coated externally with a layer of heat-insulating ceramic thinner than the metal walls of the ablative pre-cooling chamber.

14. The chill mold assembly defined in claim 9, wherein two slot-vented chill molds of different shapes are both secured to the sampling end of the lance, with a vented end of each being exposed to the hollow interior of the lance's sampling end, and each having respective open protruding portal ends converging toward a sampling zone, and wherein the ablative pre-cooling chamber surrounds the sampling zone.

15. The dual chill mold assembly defined by claim 14, wherein the sampling zone is positioned below the midpoint of the pre-cooling chamber.

* * * * *